United States Patent [19]

Geigert et al.

[11] Patent Number: 4,937,191
[45] Date of Patent: * Jun. 26, 1990

[54] STABLE HALOPEROXIDASE METHOD

[75] Inventors: John Geigert, Clayton; Te-Ning E. Liu, Martinez; Thabiso N'timkulu, Berkeley, all of Calif.

[73] Assignee: Cetus Corporation, Emeryville, Calif.

[*] Notice: The portion of the term of this patent subsequent to Nov. 7, 2004 has been disclaimed.

[21] Appl. No.: 119,825

[22] Filed: Nov. 12, 1987

Related U.S. Application Data

[63] Continuation of Ser. No. 497,654, May 24, 1983, Pat. No. 4,707,446.

[51] Int. Cl.$^5$ .......................... C12P 7/00; C12P 9/00; C12P 7/22; C12P 7/18
[52] U.S. Cl. .................................. 435/132; 435/131; 435/156; 435/157; 435/158; 435/160; 435/188; 435/189; 435/192
[58] Field of Search ................ 435/131, 132, 156, 157, 435/158, 160, 188, 189, 192

[56] References Cited

U.S. PATENT DOCUMENTS

| | | | |
|---|---|---|---|
| 4,246,347 | 1/1981 | Neidleman et al. | 435/105 |
| 4,247,641 | 1/1981 | Neidleman et al. | 435/123 |
| 4,284,723 | 8/1981 | Neidleman et al. | 435/123 |
| 4,546,080 | 10/1985 | Neidleman et al. | 435/148 |
| 4,707,446 | 11/1987 | Greigert et al. | 435/132 |
| 4,707,447 | 11/1987 | Hunter et al. | 435/132 |

FOREIGN PATENT DOCUMENTS 0099192  6/1982  Japan .................................. 435/142

OTHER PUBLICATIONS

Ishikawa, K. et al., *Chem. Abst.* vol. 95 Abst. 37873z 1981 "Partial Purification and Characterization of Peroxidas from Pellicularia".
Morrison, M., & Schonbaum, G. R., "Peroxidase-Catalyzed Halogenation", *Ann. Rev. Biochem.*, 45:861–874, 1976.
Ellis, M. B., "Dematiaceous Hyphomycetes", *Commonwealth Mycologica Institute*, Kew, Surrey, England, 1971.
Lilly, V. G., & Barnett, H. L., "Physiology of the Fungi", 1st Ed. McGraw-Hill Book Co., Inc. New York, Toronto, London, 1951.
Pansy, F. E., Basch, H., Jambor, W. P., Maestrone, G., Semar, R., & Donovick, R., "*Hamycin: In Vitro and In Vivo Studies*", Am. Soc. for Microbiol., U.S.A. 1966, p. 399.
Hager, L. P., Morris, D. R., Brown, F. S., & Eberwein, H., "Chloroperoxidase, Utilization of Halogen Anions", The J. of Biol. Chem., 241, 8, 1966. pp. 1769–1777.
Morris, D. R., & Hagers, L. P., "Chloroperoxidase, Isolation and Properties of the Crystalline Glycoprotein", vol. 241, No. 8, 1966, pp. 1763–1768.
Weissermel, K., & Arpe, H. J., "Important Raw Materials and Intermediates", Industrial Organic Chemistry, Verlag, Weinhein, New York, 1978.

*Primary Examiner*—Robin Teskin
*Attorney, Agent, or Firm*—Virginia Meyer; Jane R. McLaughlin; Albert P. Halluin

[57] ABSTRACT

A method producing a non-heme haloperoxidase which is substantially resistant to inactivation, at room temperature, in up to 0.3M $H_2O_2$ for up to 25 hours, and up to 0.5mM HOCl for up to two minutes. One such haloperoxidase, isolated from *Curvularia inaequalis*, contains about 2 gram atoms of zinc per molecule. A halogenation reaction employing the enzyme can be performed at $H_2O_2$ and hypohalous acid concentrations which produce rapid inactivation of heme-containing haloperoxidases.

18 Claims, No Drawings

STABLE HALOPEROXIDASE METHOD

This is a continuation of application Ser. No. 06/497,654, filed May 24, 1983, now U.S. Pat. No. 4,707,446.

BACKGROUND AND SUMMARY

The present invention relates to a novel haloperoxidase whose activity is substantially uninhibited by relatively high concentrations of $H_2O_2$ and hypohalous acid, and to a reaction method using such enzyme.

There has been considerable interest in recent years in enzymatic halogenation reactions. U.S. Pat. Nos. 4,247,641 and 4,284,723 describe the use of haloperoxidase enzymes to produce epoxides from alkenes. Other recent research activity in this field has explored the use of haloperoxidase enzymes to produce halogenated ketones from alkynes, alpha, gamma-halohydrins from cyclopropanes, and dihalogenated products from alkenes and alkynes.

Haloperoxidase enzymes known in the prior art which have been used in such studies include chloroperoxidase derived from the fungus *Caldariomyces fumago*, bromoperoxidase from algae, lactoperoxidase from milk, thyroid peroxidase from the thyroid, myeloperoxidase from leukocytes, and horseradish peroxidase from horseradish. These enzymes are described generally in Morrison, et al, *Ann. Rev. Biochem.*, 45, 861 (1976). Each of these known haloperoxidases is a heme-containing protein.

The term haloperoxidase is used herein to include chloroperoxidases, bromoperoxidases and iodoperoxidases enzymes. A chloroperoxidase, as that term is used herein, is an enzyme capable of oxidizing chloride, bromide, or iodide ions to the corresponding hypohalous acid, with the consumption of $H_2O_2$. A bromoperoxidase can oxidise iodide and bromide, but not chloride ions, and an iodoperoxidase can oxidize iodide ions only, both of the latter enzymes requiring $H_2O_2$ as a substrate. The hypohalous acid which is formed in a haloperoxidase reaction may react with, and halogenate, a suitable acceptor compound. Hypohalous acid may also react with halide in solution to form the corresponding halogen. The latter reaction is favored where the ratio of hypohalous acid to acceptor compound is high, and also where the solution halide is iodide.

In a haloperoxidase-catalysed halogenation reaction, both substrate $H_2O_2$ and hypohalous acid intermediate are reactive toward heme-containing haloperoxidases, and either can produce significant enzyme inactivation at elevated concentrations. It is likely that such inactivation involves a change in the oxidation state of the enzyme heme group. Enzyme inactivation by $H_2O_2$ can be minimized by performing the halogenation reaction at low $H_2O_2$ concentrations, preferably under conditions where $H_2O_2$ is generated at a low steady state level during reaction. Likewise, enzyme inactivation by hypohalous acid can be controlled by limiting the build-up of hypohalous acid in the reaction, particularly by maintaining a relatively high concentration of acceptor compound in the reaction medium. It can be appreciated that the reaction conditions necessary to minimize enzyme inactivation by $H_2O_2$ or hypohalous acid may impose serious rate limitations on the reaction and mandate careful monitoring of the reaction components during the course of the reaction. For these reasons, the usefulness of heme-containing haloperoxidases in industrial halogenation reaction applications has been limited.

Accordingly, it is an important object of the present invention to provide a method for producing a haloperoxidase which is substantially more resistant to inactivation by $H_2O_2$ and hypohalous acid than known heme-containing haloperoxidases.

A more specific object of the invention is to provide a method for producing a haloperoxidase whose activity is substantially resistant to incubation at room temperature in up to 0.3M $H_2O_2$ for up to 25 hours, and up to 0.5 mM HOCl for up to two minutes.

Providing a method for producing a stable haloperoxidase which is readily obtained by fermentation, easily isolated, has a pH optimum between about 4 and 9, and can oxidize chloride ions is still another object of the invention.

Yet another object of the invention to provide a method of using a stable haloperoxidase to oxidize halide ions in the presence of $H_2O_2$.

The invention contemplates a method for producing a haloperoxidase which is substantially resistant to levels of $H_2O_2$ and hypohalous acid which are known to produce rapid inactivation of heme-containing haloperoxidase enzymes known in the prior art. Two preferred fungal sources of the haloperoxidase are *Curvularia inaequalis*, NRRL Deposit No. 15147, and *Drechslera* sp., NRRL Deposit No. 15146. The stable haloperoxidase may be isolated readily by preparing a filtrate of fungal growth material and collecting the enzyme material which precipitates at a selected ammonium sulfate concentration.

The invention further contemplates a method of oxidizing a halide to the corresponding hypohalous acid in an enzymatic reaction which can be performed without appreciable enzyme inactivation, at $H_2O_2$ and hypohalous acid concentrations which produce rapid inactivation of known heme-containing haloperoxidases. The reaction may contain a suitable acceptor compound which is to be halogenated.

These and other objects and features of the present invention will become more fully apparent from the following detailed description of the invention.

DETAILED DESCRIPTION OF THE INVENTION

According to one aspect of the invention, a haloperoxidase whose activity is substantially unaffected by relatively high concentrations of either $H_2O_2$ or hypohalous acid is produced by selecting a microorganism which produces a non-heme haloperoxidase enzyme, and obtaining the enzyme from a culture of the microorganism. Two preferred microorganisms are *Curvularia inaequalis*, NRRL No. 15147 and *Drechslera* sp., NRRL No. 15146. Both of these fungi belong to the enteroblastic tretic group of dematiaceous hyphomycetes, according to the structure classification of dematiaceous hyphomycetes described in Ellis, M. B., *Dematiaceous Hyphomycetes*, pp. 7-23, Commonwealth Mycological Institute, Kew, Surrey, England (1971).

The selected microorganism may be cultured according to conventional techniques. For example, in culturing either of the above two fungal organisms, a small block from a sporulating slant is transferred to a modified fungal agar plate. After incubation of the seed plate, a segment of the mycelium and spores is removed and transferred to a flask containing germination broth and agar (added to prevent mycelial clumping and pellet formation). The flask is shaken for several days at room temperature. An innoculum prepared from the germination broth is transferred to a flask containing fermentation broth, and the flask is again shaken at room temperature for several days.

After a suitable growth period, the cultured microorganism is assayed for haloperoxidase activity, for example, by adding phenol red and an aliquot of freshly prepared hydrogen peroxide directly to the growth medium in the presence of a halide, such as a chloride or bromide salt. The presence of haloperoxidase is indicated by a color change from red-orange to blue-violet, indicating halogenation of the phenol red. Enzyme activity can be quantitated by following the change in absorbance of the solution spectrophotometrically at 595 nm.

Having identified the cultured organism as one which produces a haloperoxidase, a culture filtrate or other easily obtained enzyme fraction is incubated in 1% $H_2O_2$ to determine its resistance to haloperoxidase-inactivation by $H_2O_2$. At various time intervals during the incubation, which typically is performed at room temperature, the enzyme-containing fraction is assayed for haloperoxidase activity. The enzymatic chlorination of monochlorodimedon (1,1-dimethyl-4-chloro-3,5, cyclohexanedione) to dichlorodimedon in the presence of chloride ions and $H_2O_2$, described by Hager, L. P., Morris, D. R., Brown, F. S. and Eberwein, H., *J. Biol. Chem.*, 241: 1769–1777 (1966), provides a convenient enzyme assay. By way of example, the haloperoxidase activity of culture filtrate from *C. inaequalis* is resistant to inactivation by incubation in 1% $H_2O_2$ for periods up to several hours. Details are given in Example II below.

Both assays indicate the presence, in the system being tested, of an enzyme capable of catalyzing the oxidation of a halide with $H_2O_2$, to give the corresponding hypohalous acid. The hypohalous acid may further react with the halogenate selected acceptor compounds, or may react with the halide to produce the corresponding halogen.

An $H_2O_2$-stable haloperoxidase may be isolated from a selected microorganism according to standard protein-purification procedures. Example III below describes a purification of the $H_2O_2$-stable haloperoxidase from *C. inaequalis*. Briefly, this enzyme is purified by filtering fungal culture material to obtain a filtrate, and adding to the filtrate solid ammonium sulfate to produce a selected ammonium sulfate concentration. The ammonium sulfate-containing mixture is incubated at room temperature and centrifuged to remove precipitate. Additional ammonium sulfate is added to the supernatant from the centrifugation step to produce an ammonium sulfate concentration sufficient to precipitate the haloperoxidase enzyme upon incubation. After centrifugation of the ammonium sulfate mixture, the enzyme-containing pellet is resuspended in buffer.

The absence of heme in the purified enzyme is determined readily from the absorption spectrum of the enzyme in the low visible (380–500 nm) spectral region, and more particularly, in the 400–415 nm Soret-band region. Heme proteins, such as the known heme-containing haloperoxidases, show a strong, characteristic Soret-band absorption peak between about 405 and 415 nm. The absence of this peak in an $H_2O_2$-stable haloperoxidase is strong evidence that the protein does not contain stoichiometric amounts of heme.

To confirm further that the identified $H_2O_2$-stable haloperoxidase is a non-heme protein, and to investigate the possibility that the enzyme may contain a non-iron group in its active site, the metal content of the isolated haloperoxidase is determined. X-ray fluorescence analysis of *C. inaequalis* haloperoxidase, reported in Example VI below, showed that this enzyme contains less than 1 grams atom of iron per molecule. This is in contrast with the metal content of known heme-containing haloperoxidases, which contain either one or two iron atoms per molecule. Also, in contrast to known heme-containing haloperoxidases, the $H_2O_2$-stable enzyme contains a relatively high zinc content.

According to another important feature of the present invention, non-heme, $H_2O_2$-stable haloperoxidases can tolerate, without appreciable inactivation, levels of hypohalous acid which are up to two orders of magnitude greater than those which produce rapid inactivation of heme-containing haloperoxidase enzymes. A haloperoxidase enzyme produced in accordance with the above methods may be tested readily for resistance to hypohalous acid inactivation by incubating the enzyme in a solution of a relatively high concentration of hypohalous acid, such as 0.5 mM·hypochlorous acid, for increasing time periods. The resistance of the haloperoxidase isolated from *C. inaequalis* to HOCl inactivation is reported in Example V below.

In other studies conducted in support of the present application, non-heme, $H_2O_2$-stable and HOCl-stable haloperoxidases were found to be quite stable on storage, even at room temperature.

The invention also contemplates an enzymatic halogenation reaction method for halogenating a suitable acceptor compound. Typical acceptor compounds include alkenes, alkynes, cyclopropanes, beta-keto acids, cyclic beta-diketones, and aromatic ring compounds. Specific examples of organic compounds which can be halogenated via enzymatic oxidation of halide ions are well known to those skilled in the art. Alternatively, the enzyme may be employed in a reaction method for oxidizing halide ions alone, and particular iodide ions, to the corresponding molecular halogen, such as iodine.

The enzyme used in the above-mentioned reactions may be a highly purified enzyme, or a relatively impure enzyme fraction, such as the filtrate of the culture growth material. The purified or partially purified halogenating enzyme may be used in free or immobilized form. Processes for enzyme immobilization are well known, and include reacting a solution of the enzyme with one of a broad range of organic or inorganic supports. Included among these are polyacrylamide, ethylene-malelic acid copolymers, agarose, cellulose, dextran, porus glass beads, and aluminum or titanium hydroxide. Enzymes in this form have increased stability, extended life and usefulness, and recoverability. Reactions employing immobilized enzymes may be run in columns or reaction tanks.

Alternatively, the halogenating enzyme may be provided as a suspension of undisrupted cells and reacted in the form of cells immobilized on a solid support. Halogenation reactions involving an exogenous substrate (e.g. phenol red) occur readily when the substrate is added to intact cells in the presence of $H_2O_2$ and an appropriate halide salt. An important advantage of using undisrupted cells as a source of stable chloroperoxidase is that the cellular enzyme has high activity over a very broad pH range, and in particular, in the pH 9.0 range, where the activity of isolated, stable chloroperoxidases may be suboptimal. Increased enzyme stability and simplicity of enzyme preparation are other advantages in the immobilized cell reaction technique.

The haloperoxidase described herein is produced by, and obtained directly from a selected organism. The invention also contemplates a reaction method using a haloperoxidase that is produced by a microorganism, e.g., a bacterium, that has received by recombinant DNA techniques, the genetic material requisite for the synthesis of the haloperoxidase produced by the originally selected organism.

The acceptor compound to be halogenated is reacted with the enzyme in the presence of hydrogen peroxide and either chloride, bromide or iodide ions. The reaction medium preferably includes a buffer whose pH is adjusted to a selected pH between 4 and 9. Specific reaction conditions are detailed in Example VII below.

The following examples illustrate the invention, but are not intended to limit its scope.

EXAMPLE I

Detection of an $H_2O_2$-stable chloroperoxidase from *C. inaequalis*

*Curvularia inaequalis*, NRRL #15147, was identified to genus and species using the keys in the above Ellis reference. Morphological observations were made from cultured material, tweezed out on water-mounted slides, and observed through a Zeiss Universal transmitted light microscope at 500× and 1250×, as follows:

The conidiophores were acroauxic, mononematous, not nodose, and not branched at the apex. The conidiogenous cells were enteroblastic, polytretic and sympodial. The conidia were truly septate, have only transverse septa, and were generally short with more than 3 septa, sometimes curved and had end cells frequently paler than the intermediate cells. These observations fit the general description of the Curvularia genus, according to Ellis, cited above.

*Curvularia inaequalis* was speciated on the basis of the following microscopic observations of the conidia: The hilium of the conidia was not protuberant. The conidia were smooth-walled, predominantly 4-septate, and not uncinate. They averaged between 30 and 45 microns in length and were less than 17 microns thick. The conidia frequently appeared straight, but a few were slightly curved, tapering a little at each end. The conidia matched the one illustrated in FIG. 323D, on page 455 of the Ellis reference.

A small block from a sporulating slant of *C. inaequalis*, NRRL #15147, was aseptically cut out and placed face down on the dry surface of modified fungal agar (Barnett and Lilly, *Physiology of the Fungi* (1951)). The fungal agar was prepared by adding glucose (15.0 g.), yeast extract (3.0 g.), agar (20.0 g.), artificial sea water (1 ml; Aquarium Systems, Eastlake, Ohio) to 999 ml of distilled water. After autoclaving at 15 psi for 15 minutes, thiamin (100 micrograms) and biotin (5 micrograms) were added via filter sterilization. The final pH was between 6.0 and 6.5.

The seed plates were incubated at 25° C. for 3 to 7 days. A segment of mycelium and spores was transferred aseptically to a 125 ml Erlenmeyer flask containing 25 ml of germination broth which consisted of: tryptone (5.0 g)., malt extract (3.0 g), glucose (10.0 g), and yeast extract (3.0 g) per liter of distilled water (Pansey et al., *Antimicrob. Agents Chemother.*, 399 (1966)). Agar (0.2 g per liter) was added to prevent mycelial clumping and pellet formation.

The flask was shaken on a New Brunswick rotary shaker for 3 to 5 days at 200 rpm in a 25° C. room. If a gelatinous pellet formed on incubation, the material was harvested and ground aseptically to applesauce consistency in a sterile Waring Blender for 5–30 seconds in short (5 second) bursts. The growth material was diluted with sterile distilled water to form a 5% (v/v) inoculum.

Inoculum was transferred aseptically to 15 ml of fermentation broth contained in a 125 Erlenmeyer flask. The fermentation broth was identical to the germination broth, but contained no agar. The flask was shaken at 200 rpm on a New Brunswick rotary shaker at 25° C. The fungal growth solution was assayed for haloperoxidase activity in the flask after 5 to 9 days of incubation.

A phenol red reagent used to detect haloperoxidase activity was prepared by adding 40 ml of 0.2% phenol red in 95% ethanol to one liter of 0.3M $KPO_4$ and 0.5M KBr. The pH was adjusted to 7.0 with KOH. The phenol red reagent was added directly to an equal volume of growth material from the flask. Freshly prepared hydrogen peroxide was added to a final concentration of 0.03% to start the reaction. Haloperoxidase activity was indicated by a color change from red-orange to blue-violet. The reaction was performed at room temperature.

After a 1 hour reaction period, the reaction mixture was centrifuged to remove fungal cells. The optical density of the reaction mixture supernatant was determined against a blank which was identical to the sample, but contained no phenol red. The optical density reading at 595 nm was greater than about 1.2.

EXAMPLE II

Resistance of unfractionated *C. inaequalis* haloperoxidase to inactivation by 1% $H_2O_2$ Fungal growth material obtained by culturing *C. inaequalis* according to Example I was disrupted by sonication and filtered through Whatman No. 1 filter paper at room temperature, to produce a crude filtrate containing the haloperoxidase enzyme. The filtrate was incubated at room temperature in the presence of 1% (about 0.3M) $H_2O_2$ for increasing time periods up to 100 hours. At selected time intervals, an aliquot of the filtrate was removed and assayed for its ability to chlorinate monochlorodimedon, according to the method referenced above. The enzyme showed no loss of activity (measured as activity units per filtrate volume) over the 100 hour period of incubation in 1% $H_2O_2$.

EXAMPLE III

Purification of *C. inaequalis* haloperoxidase

A crude filtrate was obtained, as above, by filtering *C. inaequalis* growth material sonicate through Whatman No. 1 filter paper. Solid ammonium sulfate was added to the filtrate to bring the filtrate to 40% saturated ammonium sulfate at room temperature. The filtrate-ammonium sulfate mixture was incubated at room temperature for about a half hour, then centrifuged at 10,000 rpm for 90 minutes at 4° C., and the precipitate discarded. Additional ammonium sulfate was added to the supernatant to produce a 55% saturated ammonium sulfate solution at room temperature. The resulting mixture was incubated at room temperature for one half hour, then centrifuged as described above. The supernatant was discarded and the precipitate (containing the haloperoxidase) was resuspended in 9 volumes of 0.1M phosphate buffer, pH 6. The enzyme suspension was incubated overnight at 4° C., and the suspension was centrifuged as described above. The supernatant fluid containing the haloperoxidase was then used immediately, or stored at −20° C.

The purity of the ammonium sulfate-fractionated haloperoxidase was examined by sodium dodecyl sulfate polyacrylamide gel electrophoresis (SDS-PAGE), according to a standard procedure. The haloperoxidase sample showed a single major band, with minor contaminating proteins. The major band had an estimated molecular weight of about 66,000 daltons, based on its migration distance with respect to known molecular weight markers.

The partially purified haloperoxidase was further purified by column chromatography on DEAE-sepharose. The column volume was 157 ml, and the sample size was 33 ml. The buffer gradient ranged from 50 mM phosphate buffer, pH 6.0, to 500 mM phosphate buffer, pH 6.0, in a total buffer gradient volume of about 600 ml. The enzyme eluted at a buffer concentration of about 400 mM phosphate buffer. The haloperoxidase fraction obtained was concentrated and examined by SDS-PAGE. A single major band with minor contaminants was observed.

The haloperoxidase was purified substantially to homogeniety by molecular sieve column chromatography, using Sephacryl-300. The column was calibrated with several known molecular weight markers. Based on the elution volume from the column, the estimated molecular weight of the intact protein is about 260,000 daltons.

The purified haloperoxidase sample thus obtained was concentrated, and a portion was analyzed by SDS-PAGE. A single band corresponding to a (subunit) molecular weight of around 66,000 was observed. The intact and subunit molecular weights obtained indicate that the haloperoxidase is a tetramer composed of four equal-size subunits, each of about 66,000 dalton molecular weight.

EXAMPLE IV

Resistance of purified *C. inaequalis* haloperoxidase to inactivation by $H_2O_2$ As described in Example I, the haloperoxidase activity of culture filtrate from *C. inaequalis* showed substantially no inactivation by incubation in 1% $H_2O_2$ at room temperature, for incubation periods up to 100 hours. A similar type of experiment was performed to determine the resistance of purified haloperoxidase to inactivation by $H_2O_2$. Briefly, a sample of the purified enzyme was incubated in the presence of 1% $H_2O_2$ at room temperature. At varying time intervals up to 100 hours, an aliquot of the $H_2O_2$-containing sample was removed and its ability to chlorinate monochlorodimedon was determined, as previously described. There was no observed loss of chloroperoxidase activity with incubation times up to about 25 hours. After about 25 hours, a steady decline in haloperoxidase activity was measured, with about a 50% loss in activity (measured as activity units per sample volume) after 100 hours of incubation in 1% $H_2O_2$. The apparently greater $H_2O_2$-resistance of haloperoxidase from crude filtrate, as reported in Example I, probably reflects the fact that, in the crude filtrate incubate, a slow decomposition of added $H_2O_2$ occurs, reducing the $H_2O_2$ level to which the enzyme in the crude filtrate is exposed.

In parallel studies, it was found that the fungal chloroperoxidase derived from *C. fumago* was significantly inactivated by incubation at room temperature in 0.01% $H_2O_2$ within an incubation period of less than an hour, where the $H_2O_2$ was maintained at a substantially constant 0.01% level.

EXAMPLE V

Resistance of purified *C. inaequalis* haloperoxidase to inactivation by HOCl

A sample of the purified enzyme from Example III was incubated in HOCl, at the HOCl concentrations shown in column 1 in TABLE I below. The incubations were performed at room temperature. After two or five minute incubation periods, as indicated in column 2 of the table, an aliquot of the sample was removed and its activity in chlorinating monochlorodimedon, according to the above-described assay procedure, was determined. The activity is expressed in activity units per ml of incubation medium in column 3 of the table, and as percent of original chloroperoxidase activity in column 4. Some of the data values represent the average of two independently measured values.

TABLE I

| 1<br>[HOCl]<br>(mM) | 2<br>time<br>(minutes) | 3<br>A.U./ml | 4<br>activity |
|---|---|---|---|
| 0.0 | 0 | 2.87 | 100% |
| 0.5 | 2 | 2.18 | 75% |
| 0.5 | 5 | 1.81 | 63% |
| 0.88 | 2 | 1.6 | 56% |
| 4.28 | 2 | .78 | 27% |
| 4.28 | 5 | .05 | 29% |
| 6.67 | 5 | .025 | 1% |

For purposes of comparison, a similar experiment was performed to measure the inactivation by HOCl of purified chloroperoxidase obtained from *C. fumago*. As discussed above, the *C. fumago* chloroperoxidase is a heme-containing protein which is relatively susceptible to inactivation by $H_2O_2$. The presentation of the data in TABLE II follows that in TABLE I.

TABLE II

| 1<br>[HOCl]<br>(mM) | 2<br>time<br>(minutes) | 3<br>A.U./ml | 4<br>activity |
|---|---|---|---|
| 0.0 | 0 | 2.28 | 100% |
| 0.005 | 2 | 0.938 | 41% |
| 0.05 | 2 | 0.573 | 25% |
| 0.5 | 2 | 0.041 | 2% |

The chloroperoxidase enzyme obtained according to the method of the present invention is thus shown to be more than two orders of magnitude more resistant to inactivation by hypohalous acid than the *C. fumago* chloroperoxidase.

EXAMPLE VI

Metal content of purified *C. inaequalis* haloperoxidase

The absorption spectrum of purified *C. inaequalis* haloperoxidase between 250 and 800 nm was measured conventionally at three different protein concentrations. All three protein concentrations gave a strong absorption peak at about 280 nm, characteristic of protein, but showed no absorption peak between 300 nm and 800 nm. In particular, even at the highest concentration of haloperoxidase which was studied, there was no indication of an absorption peak in the Soret-band region between about 400 and 415 nm. By contrast, chloroperoxidase derived from *C. fumago*, myeloperoxidase from leukocytes, horseradish peroxidase from horseradish, and lactoperoxidase from milk all showed strong Soret-band absorption peaks.

The metal content of the purified *C. inaequalis* haloperoxidase was determined by a conventional X-ray fluorescense technique. The metal content of the *C. inaequalis* stable haloperoxidase (SHPO) was compared with that of lactoperoxidase from milk (LPO), chloroperoxidase from *C. fumago* (CPO), myeloperoxidase from leukocytes (MPO) and horseradish peroxidase from horseradish (HRP). The five enzymes were analyzed for manganese, iron, zinc and nickel. The measured metal-content values are shown in Table III, expressed in gram atoms per molecule. A dash entry indicates undetectable metal content.

TABLE III

| Enzyme | Mn | Fe | Zn | Ni |
|---|---|---|---|---|
| SHPO | 0.15 | 0.7 | 2.2 | — |
| LPO | — | 0.98 | 0.17 | 0.09 |
| CPO | 0.026 | 1.66 | 0.09 | — |
| MPO | — | 1.94 | 0.44 | — |
| HRP | — | 0.97 | 0.57 | 0.04 |

Unlike the known heme-containing haloperoxidases examined, the $H_2O_2$-stable haloperoxidase contained significantly less than 1 gram atom of iron per molecule, itself a tetramer. On the other hand, the enzyme has a zinc content which is substantially greater than that observed for any of the other 4 haloperoxidases which were studied. The data in Table III suggest that the purified fungal haloperoxidase contains about 2 zinc atoms per tetramer.

EXAMPLE VII

Chlorination reactions using purified *C. inaequalis* haloperoxidase

A reaction mixture containing 30 mM potassium chloride, 0.3M potassium phosphate buffer, pH 5.0, 10 mM $H_2O_2$ and 20 mM monochlorodimedon was prepared. To 10 ml of the reaction mixture in a 25 ml Pyrex flask, was added purified *C. inaequalis* haloperoxidase, corresponding to 16 monochlorodimedon units. The reaction was carried out over a period of up to six hours at room temperature.

The reaction was followed spectrophotometrically by the conversion of monochlorodimedon, which has a strong absorption at 292 nm, to dichlorodimedon which has a very weak absorption at this wavelength.

To verify that the $H_2O_2$-stable haloperoxidase is resistant to $H_2O_2$ and hypohalous acid inactivation in a chlorination reaction, the above monochlorodimedon chlorination reaction was performed at an initial $H_2O_2$ concentration of 0.3M. The rate of conversion of monochlorodimedon to dichlorodimedon observed was significantly less than that in the reaction containing an initial 20 mM $H_2O_2$ concentration, indicating substrate inhibition at high $H_2O_2$ levels. In fact, further studies showed that the optimal $H_2O_2$ concentration, at the above enzyme and reaction mixture concentrations, is about 0.1 mM $H_2O_2$. Thus, levels of $H_2O_2$ in the 0.3M range can be expected to inhibit enzyme activity significantly.

Nonetheless, no reduction in enzyme activity over the several-hour period of the reaction was observed, confirming that the enzyme was substantially resistant to inactivation by high levels of $H_2O_2$ and to HOCl generated in the reaction. By contrast, chloroperoxidase from *C. fumago* was rapidly and substantially completely inactivated in a reaction mixture containing 0.3M $H_2O_2$.

EXAMPLE VIII

Chlorination of allyl chloride by *C. inaequalis* haloperoxidase

A reaction medium containing 30 mM KCl, 0.3M $KPO_4$ buffer, pH 5.5, 10 mM $H_2O_2$ and 20 mM allyl chloride (Aldrich Chemical Company, Milwaukee, WI) was prepared. To 10 ml of the reaction mixture in a 25 ml Pyrex flask was added the chloroperoxidase isolated as above from *C. inaequalis*, NRRL #15147, corresponding to 16 monochlorodimedon units, as defined in Hager, cited above. The reaction was carried out for 5 hours at room temperature.

The reaction products were identified by gas chromatography-mass spectrometry (GCMS). Ten (10) microliters of the reaction mixture were injected into a Finnigan 4021 GCMS equipped with a 6 foot×4 mm coiled, glass column packed with Tenax-GC (80/100 mesh). Flow rate through the column was set at 30 ml/minute of helium. The column temperature was 190° C. The mass spectrometer was operated at 70 ev electron impact ionization.

The products were quantitated by gas chromatography (GC) using flame ionization detection (FID). Five (5) microliters of the reaction mixture was injected into a Variam 3700 GC, equipped with a 6 foot×4 mm coiled glass column packed with Tenax-GC (80/mesh). Flow rate through the column was set at 40 ml/minute of helium. The temperature conditions were identical to those above.

Of the two products observed by GCMS, one had a GC retention time of 5 minutes and showed the mass spectrum diagnostic for 1,3-dichloro-2-propanol, as confirmed by GC retention time and mass spectrum of an authentic sample of 1,3-dichloro-2-propanol (purchased from Aldrich Chemical Company).

The other product had a GC retention time of 6 minutes and showed the mass spectrum diagnostic for 2,3-dichloro-1-propanol, as confrimed by the GC retention time and mass spectrum of an authentic sample of 2,3-dichloro-1-propanol (purchased from Aldrich Chemical Company). Quantitation of the products showed that 1,3-dichloro-2-propanol and 2,3-dichloro-1-propanol products constituted about 54% and 46%, respectively, of the total yield (about 4.1 mg). Both products were converted to epichlorohydrin by addition of lime to the aqueous reaction mixture until the pH was greater than 10. Identity of epichlorohydrin was confirmed by gas chromatography-mass spectrometry comparison with an authentic epichlorohydrin sample (purchased from Aldrich Chemical Company). Similar results were obtained at pH 5.0 and 6.0.

EXAMPLE IX

Chlorination of allyl alcohol by *C. inaequalis* haloperoxidase in the presence of sea water A reaction medium containing seawater (collected off the Monterey, Calif. coast) at a final chloride concentration of 400 mM, 0.3M $KPO_4$, pH 5.0, 10 mM $H_2O_2$ and 24 mM allyl alcohol (Aldrich Chemical Company) was prepared. Chlorination of substrate by *C.*

*inaequalis*, NRRL #15147, chloroperoxidase was performed under the conditions described in Example VIII.

Three products were detected. Of these, one product has a GC retention time of 6 minutes and showed the mass spectrum diagnostic for 2,3-dichloro-1-propanol, identical to that of an authentic sample of 2,3-dichloro-1-propanol. Two other products had GC retention times of 7 and 8 minutes, and showed the mass spectra diagnostic for chloropropanediols. The product having a 7 minute retention time was identified as 1-chloro-2,3-propanediol by mass spectrographic analysis. The product having an 8 minute retention time was identified as 2-chloro-1,3-propanediol. The relative percentages of 2,3-dichloro-1 C-propanol, 1-chloro-2,3-propanediol and 2-chloro-1,3-propanediol produced in the reaction were 82%, 10% and 8%, respectively.

As a further confirmation of the identities of the products, 2,3-dichloro-1-propanol was converted to epichlorohydrin by addition of lime to the aqueous reaction mixture until the pH was greater than 10. Identity of epichlorohydrin was confirmed by gas chromatography-mass spectrometry comparison with an authentic sample. The two chloro-propanediols were converted to glycidol by addition of lime to the aqueous reaction mixture until the pH was greater than 10. Identity of glycidol was confirmed by gas chromatography-mass spectrometry comparison with an authentic sample (purchased from Aldrich Chemical Company).

EXAMPLE X

A reaction medium containing seawater was prepared as in Example IX, except that KBr was added to a final concentration of 100 mM. Upon reaction with the *C. inaequalis* chloroperoxidase, under conditions like those in Example IX, the following products were obtained from allyl alcohol: 3-chloro-2-bromo-1-propanol; 3-bromo-2-chloro-1-propanol; 2,3-dichloro-1-propanol; 2,3-dibromo-1-propanol; and chloro and bromo propanediols.

EXAMPLE XI

Reactions similar to those described in Examples IX and X were carried out in unbuffered seawater (pH 7.49) and unbuffered seawater spiked with 100 mM KBr. The products obtained were the same of those obtained in Examples IX and X, respectively.

EXAMPLE XII

Oxidation of iodide ions to molecular iodine

A reaction medium containing potassium iodide at a final iodide concentration of about 80 mM, 0.1KPO$_4$ buffer, pH 7.0, and H$_2$O$_2$ at a final concentration of about 8 mM was prepared. To 5 ml of the reaction mixture in a 25 ml Pyrex flask was added haloperoxidase enzyme isolated as above from *C. inaequalis*, NRRL #15147, corresponding to 16 monochlorodimedon units. The reaction was carried out for 1 hour at room temperature and pressure, and after which 10 ml chloroform was added to the reaction flask. After shaking, the violet coloration of the chloroform layer due to dissolved iodine was measured spectrophotometrically at 510 nm. Iodine standards were prepared by dissolving known amounts of iodine (Baker Chemical Company, 99.9% pure) in chloroform. The amount of iodine produced in the reaction was about 8.2 mg.

Product identity was confirmed by injecting 10 microliters of the reaction mixture into a Finnigan Model 4021 gas chromatograph/mass spectrometer/data system, equipped with a 6 foot×¼ inch coiled, glass column, packed with Tenax-GC (60/80 mesh). Carrier gas (helium) flow rate was set at 25 ml/minute. The column temperature was programmed from 100° C. to 250° C. at a rate of 10° C./minute. The mass spectrometer was set on electron impact ionization mode, 70 eV. Iodine eluted from the column near 200° C., and had a characteristic mass spectrum: 2 single peaks of high abundance, m/e 127 and m/e 254.

EXAMPLE XIII

Method of producing an H$_2$O$_2$-stable haloperoxidase from Drechslera, sp., NRRL Deposit No. 15146

This example illustrates another application of the method of the invention for producing an H$_2$O$_2$-stable haloperoxidase.

Drechslera sp., NRRL #15146 was identified to genus according to morphological characteristics which were as follows:

The conidiophores were acroauxic, mononematous, not nodose, and not branched at the apex. The conidiogeneous cells were enteroblastic, polytretic, and sympodial. The conidia were pseudoseptate with transverse pseudosepta only. The conidia were usually fusiform to cylindrical in shape. These characteristics fit within the general description of the genus Drechslera, according to Ellis, cited above. The fungal host was not known, and therefore the organism could not be identified as to species.

A fungal growth culture of the organism was prepared substantially according to the method described in Example I for the preparation of the *C. inaequalis* fungal growth culture. A haloperoxidase was detected by the ability of cultured cells to brominate phenol red at a pH between about 7 and 8. The Drechslera haloperoxidase, contained in a culture growth material filtrate, was incubated in the presence of 220 mM H$_2$O$_2$ for up to 18 hours at room temperature without a detectable loss in its ability to brominate phenol red. Based on this result, the enzyme was identified as a stable haloperoxidase according to the present invention.

The haloperoxidase from the selected Drechslera was partially purified by an ammonium sulfate precipitation procedure essentially identical to that described in Example III for the purification of *C. inaequalis* haloperoxidase. The partially purified enzyme exhibited no absorption peak(s) in the visible region, and in particular, in the Soret-band absorption region, indicating that the haloperoxidase is a non-heme protein.

From the foregoing, it can be appreciated how various objects of the invention are met. The haloperoxidase enzymes produced according to the present invention are substantially more resistant (in one case, more than two orders of magnitude more resistant) to H$_2$O$_2$ and hypohalous acid than heme-containing haloperoxidases, such as the chloroperoxidase from *C. fumago*, which have been described heretofore. The enzyme can thus be used in commercial halogenation reactions carried out over long periods, at maximal reaction rates, and without the requirement for monitoring reactant concentrations carefully to limit buildup of hypohalous acid.

An hypohalous acid-resistant haloperoxidase can be produced readily, according to the invention, by selecting a microorganism which is capable of brominating phenol red, and which produces a soluble enzyme which is not inactivated by extended incubation in up to 1% $H_2O_2$. Alternatively, the desired non-heme haloperoxidase can be identified readily by the absence of a Soret-band absorption peak in the visible region.

Two selected fungal microorganisms which produce a stable, non-heme haloperoxidase are described herein. The fungal enzymes can be obtained in large quantities by relatively inexpensive fermentation techniques. For each fungal source, the stable non-heme haloperoxidase is easily obtained in partially purified form by filtration and protein-precipitation methods which are well suited to large-scale preparation.

While the invention has been described with particular reference to specific examples, it will be understood that these examples are in no way intended to limit the scope of the invention. Various changes and modifications may be made without departing from the spirit of the invention.

What is claimed is:

1. A non-heme haloperoxidase produced by a fungus of the dematiaceous hyphomycetes selected from the genera consisting of Curvularia and Dreschlera, said haloperoxidase having an activity that is resistant to inactivation by incubation in up to 0.3M $H_2O_2$ for up to 25 hours at room temperature and by incubation in up to 0.5 mM HOCl for up to two minutes at room temperature.

2. The haloperoxidase of claim 1, wherein said haloperoxidase is stable when used in a hypohalous acid generating reaction system containing up to about 0.1M $H_2O_2$.

3. The haloperoxidase of claim 1 wherein said haloperoxidase is substantially resistant to inactivation by incubation in $H_2O_2$ or HOCl at concentrations thereof known to produce rapid inactivation of haloperoxidase from *Caldariomyces fumago*.

4. The haloperoxidase of claim 1, wherein said haloperoxidase is derived from a fungus selected from the group consisting of *Curvularia inaequalis*, NRRL Deposit No. 15147 and Drechslera sp., NRRL Deposit No. 15146.

5. A method of producing a halogenating enzyme whose haloperoxidase activity is substantially resistant to inactivation by incubation in up to 0.3M $H_2O_2$ for up to 25 hours at room temperature, and by incubation in up to 0.5 mM HOCl for up to two minutes at room temperature, said method comprising:
   selecting a microorganism of dematiaceous hyphomycetes which is selected from the genera consisting of Curvularia and Drechslera and which microorganism produces a non-heme enzyme capable of brominating phenol red in the presence of $H_2O_2$ and bromide, and
   obtaining the non-heme enzyme from a culture of the selected microorganism.

6. A method of producing a haloperoxidase enzyme which is stable when used in a hypohalous acid-generating reaction system containing up to about 0.1M $H_2O_2$, said method comprising:
   selecting a microorganism of dematiaceous hyphomycetes which is selected from the group consisting of Curvularia and Drechslera and which microorganism produces a non-heme enzyme capable of brominating phenol red in the presence of $H_2O_2$ and bromide, and
   obtaining the non-heme enzyme from a culture of the selected microorganism.

7. A method of producing a haloperoxidase enzyme which is substantially resistant to inactivation by incubation in $H_2O_2$ or HOCl, at concentrations thereof known to produce rapid inactivation of haloperoxidase from *Caldariomyces fumago*, said method comprising:
   selecting a microorganism of dematiaceous hyphomycetes capable of brominating phenol red in the presence of $H_2O_2$ and bromide,
   identifying the selected microorganism as one which produces a non-heme haloperoxidase which is substantially resistant to inactivation by incubation in the presence of up to $0.7H_2O_2$ for up to 25 hours at room temperature, and
   obtaining the haloperoxidase enzyme from a culture of the selected, identified microorganism.

8. The method of claim 5, wherein said selecting includes measuring the absorbance of a haloperoxidase-containing fraction from the organism in the 400–415 nm spectral region.

9. The method of claim 5, wherein said microorganism is selected from the group which includes *Curvularia inaequalis*, NRRL Deposit No. 15147 and Drechslera sp., NRRL Deposit No. 15146.

10. The method of claim 9, wherein said obtaining includes preparing a filtrate of culture growth material, fractionating the filtrate by ammonium sulfate precipitation, and collecting the enzyme fraction which precipitates between about 40% and 55% saturated ammonium sulfate.

11. The method of claim 5, wherein the non-heme enzyme is a soluble, zinc-containing enzyme.

12. The method of claim 6, wherein said selecting includes measuring the absorbance of a haloperoxidase-containing fraction from the organism in the 400–415 nm spectral region.

13. The method of claim 6, wherein the microorganism is selected from the group which includes *Curvularia inaequalis*, NRRL Deposit No. 15147, and Drechslera sp., NRRL Deposit No. 15146.

14. The method of claim 13, wherein said obtaining includes preparing a filtrate of culture growth material, fractionating the filtrate by ammonium sulfate precipitation, and collecting the enzyme fraction which precipitates between about 40% and 55% saturated ammonium sulfate.

15. The method of claim 6, wherein the microorganism selected is *Curvularia inaequalis*, and the non-heme enzyme produced thereby is a soluble, zinc-containing enzyme whose activity is substantially uninhibited by preincubation in $H_2O_2$ or hypochlorous acid, at concentrations thereof which are more than two orders of magnitude greater than those known to inactivate the chloroperoxidase isolated from *Caldariomyces fumago*.

16. The method of claim 7, wherein said microorganism is selected from the group which includes *Curvularia inaequalis*, NRRL Deposit No. 15147 and Drechslera sp., NRRL Deposit No. 15146.

17. The method of claim 16, wherein said obtaining includes preparing a filtrate of culture growth material, fractionating the filtrate by ammonium sulfate precipitation, and collecting the enzyme fraction which precipitates between about 40% and 55% saturated ammonium sulfate.

18. The method of claim 7, wherein the selected microorganism produces a soluble, zinc-containing haloperoxidase.

* * * * *